(12) United States Patent
Dede

(10) Patent No.: US 11,801,848 B2
(45) Date of Patent: Oct. 31, 2023

(54) ELECTRONIC SKIN FOR VEHICLE COMPONENTS

(71) Applicant: Toyota Motor Engineering & Manufacturing North America, Inc., Plano, TX (US)

(72) Inventor: Ercan Mehmet Dede, Ann Arbor, MI (US)

(73) Assignee: Toyota Motor Engineering & Manufacturing North America, Inc., Plano, TX (US)

(*) Notice: Subject to any disclaimer, the term of this patent is extended or adjusted under 35 U.S.C. 154(b) by 812 days.

(21) Appl. No.: 16/523,074

(22) Filed: Jul. 26, 2019

(65) Prior Publication Data
US 2021/0024078 A1 Jan. 28, 2021

(51) Int. Cl.
*B60W 50/00* (2006.01)
*B60R 13/02* (2006.01)
(Continued)

(52) U.S. Cl.
CPC ....... *B60W 50/0098* (2013.01); *A61B 5/0002* (2013.01); *A61B 5/01* (2013.01);
(Continued)

(58) Field of Classification Search
CPC .................................................. B60W 50/0098
See application file for complete search history.

(56) References Cited

U.S. PATENT DOCUMENTS 9,082,239 B2 7/2015 Ricci
9,466,161 B2 * 10/2016 Ricci ................. A61B 5/6808
(Continued)

FOREIGN PATENT DOCUMENTS

CN 105270292 A * 1/2016 ............. B60K 37/06
WO WO-2014010568 A1 * 1/2014 ........... A61B 5/0051

OTHER PUBLICATIONS

Park, Minhoon, MoS2-Based Tactile Sensor for Electronic Skin Applications, Wiley Online Library, https://doi.org/10.1002/adma.201505124 (Feb. 2, 2016)(hereinafter "Park").*
(Continued)

*Primary Examiner* — Jean Paul Cass
(74) *Attorney, Agent, or Firm* — Christopher G. Darrow; Darrow Mustafa PC

(57) ABSTRACT

Systems and methods are provided for adjusting a control of a vehicle system based on a condition of an occupant. The system includes a replaceable or upgradeable electronic skin removably coupled to an interior vehicle component. The electronic skin includes at least one sensor positioned therein, configured to monitor/obtain a biometric, physiological, or wellness condition measurement from an occupant. The system includes one or more processors and a memory communicably coupled thereto. An occupant comfort module is provided including instructions that, when executed, collect and monitor feedback from the at least one sensor; determine that the feedback exceeds a predetermined threshold; and determine an adjustment for a vehicle system based on the feedback. A control module may be provided including instructions that, when executed by the one or more processors, cause the vehicle system to change at least one setting based on the adjustment determined by the occupant comfort module.

20 Claims, 7 Drawing Sheets

(51) Int. Cl.
| | |
|---|---|
| *B60N 2/00* | (2006.01) |
| *B60R 16/023* | (2006.01) |
| *B60H 1/00* | (2006.01) |
| *B60Q 3/80* | (2017.01) |
| *B60G 17/019* | (2006.01) |
| *B60G 17/0195* | (2006.01) |
| *B60N 2/02* | (2006.01) |
| *B60W 50/14* | (2020.01) |
| *G07C 5/08* | (2006.01) |
| *A61B 5/00* | (2006.01) |
| *A61B 5/0205* | (2006.01) |
| *A61B 5/01* | (2006.01) |
| *A61B 5/1455* | (2006.01) |
| *B60N 2/75* | (2018.01) |
| *A61B 5/021* | (2006.01) |
| *A61B 5/08* | (2006.01) |

(52) U.S. Cl.
CPC ...... *A61B 5/02055* (2013.01); *A61B 5/14551* (2013.01); *A61B 5/4266* (2013.01); *A61B 5/6893* (2013.01); *B60G 17/019* (2013.01); *B60G 17/0195* (2013.01); *B60H 1/00742* (2013.01); *B60N 2/002* (2013.01); *B60N 2/0244* (2013.01); *B60Q 3/80* (2017.02); *B60R 13/02* (2013.01); *B60R 13/0243* (2013.01); *B60R 16/0231* (2013.01); *B60W 50/14* (2013.01); *G07C 5/0808* (2013.01); *A61B 5/021* (2013.01); *A61B 5/0816* (2013.01); *A61B 2562/0247* (2013.01); *A61B 2562/046* (2013.01); *B60G 2400/204* (2013.01); *B60G 2400/82* (2013.01); *B60G 2400/84* (2013.01); *B60N 2/75* (2018.02); *B60R 2013/0287* (2013.01); *B60W 2050/143* (2013.01); *B60W 2050/146* (2013.01); *B60W 2520/10* (2013.01); *B60W 2540/22* (2013.01); *B60W 2552/00* (2020.02); *B60W 2554/00* (2020.02); *B60W 2555/20* (2020.02)

(56) References Cited

U.S. PATENT DOCUMENTS

| | | | | |
|---|---|---|---|---|
| 10,349,892 | B2* | 7/2019 | Song | B60N 2/002 |
| 10,967,871 | B1* | 4/2021 | Marti | B60W 50/16 |
| 2008/0243329 | A1* | 10/2008 | Hamel | B62D 5/0481 |
| | | | | 701/31.4 |
| 2014/0306826 | A1* | 10/2014 | Ricci | G01C 21/26 |
| | | | | 340/573.1 |
| 2017/0162072 | A1* | 6/2017 | Horseman | A61B 5/6803 |
| 2018/0014734 | A1 | 1/2018 | Rogers et al. | |
| 2019/0315372 | A1* | 10/2019 | Chen | B60H 1/2226 |
| 2019/0375382 | A1* | 12/2019 | Nakatsuka | B60W 30/18109 |
| 2021/0024078 | A1* | 1/2021 | Dede | B60Q 3/80 |
| 2021/0138232 | A1* | 5/2021 | Paz | A61N 1/36031 |
| 2021/0291619 | A1* | 9/2021 | Aghniaey | B60H 1/00971 |
| 2022/0036101 | A1* | 2/2022 | Gupta | G06V 20/597 |

OTHER PUBLICATIONS

Nabar, B.P. et al., "Self-powered, tactile pressure sensing skin using crystalline ZnO nanorod arrays for robotic applications," Sensors (2013) IEEE, 1 page Abstract (https://ieeexplore.ieee.org/document/6688347/authors).

Ell, "Development of software and smart seat with built-in sensors for comfort and safety,"EESTI Innovatsiooni Instituut (2017) 3 pages (http://www.eii.ee/development-of-software-and-smart-seat-with-built-in-sensors-for-comfort-and-safety/.

Bosch, "Automotive MEMS sensors—Seat comfort systems," Bosch Semiconductors (2018) 4 pages (http://www.bosch-semiconductors.com/automotive-mems-sensors/seat-comfort-systems/).

Makarov, D. et al., "Shapeable magnetoelectronics," Appl. Phys. Rev., 3, 011101 (2016) 25 pages.

Khan, Y. et al., "A flexible organic reflectance oximeter array," PNAS Latest Articles (2018) 10 pages (www.pnas.org/cgi/doi/10.1073/pnas.1813053115).

Choi, S. et al., "Highly conductive, stretchable and biocompatible Ag-Au core-sheath nanowire composite for wearable and implantable bioelectronics," Nature Nanotechnology, vol. 13 (2018) pp. 1048-1056.

Gao, W. et al., "Fully integrated wearable sensor arrays for multiplexed in situ perspiration analysis," vol. 529 (2016) pp. 509-526.

Gao, Y. et al., "Wearable Microfluidic Diaphragm Pressure Sensor for Health and Tactile Touch Monitoring," Adv. Mater., vol. 29 (2017), 8 pages.

Kweon, O.Y. et al., "Wearable high-performance pressure sensors based on three-dimensional electrospun conductive nanofibers," NPG Asia Materials 10 (2018) pp. 540-551.

Lopes, P.A. et al., "Hydroprinted Electronics: Ultrathin Stretchable Ag-In-Ga E-Skin for Bioelectronics and Human-Machine Interaction," ACS Appl Mater Interfaces, vol. 10 (2018) pp. 38760-38768.

Park, Y.L. et al., "Design and Fabrication of Soft Artificial Skin Using Embedded Microchannels and Liquid Conductors," IEEE Sensors Journal, vol. 12, No. 8 (2012) pp. 2711-2718.

Selvam, A.P. et al., "A wearable biochemical sensor for monitoring alcohol consumption lifestyle through Ethyl glucuronide (EtG) detection in human sweat," Sci Rep. 6, 23111; doi: 10.1038/srep23111 (2016) pp. 1-11.

Wang, C. et al., "Monitoring of the central blood pressure waveform via a conformal ultrasonic device," Nature Biomedical Engineering, vol. 2 (2018) pp. 687-695.

Jeon, J. et al., Flexible Wireless Temperature Sensors Based on Ni Microparticle-filled Binary Polymer Composites, Adv. Mater. 25 (2013) pp. 850-855.

* cited by examiner

ELECTRONIC SKIN FOR VEHICLE COMPONENTS

TECHNICAL FIELD

The present disclosure generally relates to shapeable materials incorporated with sensors and, more particularly, to various vehicle components including removable/upgradeable, flexible skins with sensors for monitoring occupant biometric data and controlling vehicle systems based on the same.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Vehicle designs are increasingly taking into account the comfort and well-being of occupants as consideration for providing a favorable user experience. Vehicles are being provided with numerous safety, comfort, and convenience features that can be customized for individual occupants. Such features include zoned heating and cooling, variable suspension systems, adjustable interior and exterior lighting, state-of-the-art acoustic systems, ergonomic seating, and the like. These features are commonly manually controlled, however, and may distract an occupant when settings are changed.

Accordingly, it would be desirable to provide improved automated controls of various vehicle systems and features, to minimize distraction to an occupant and provide a more favorable user experience.

SUMMARY

This section provides a general summary of the disclosure and is not a comprehensive disclosure of its full scope or all of its features.

In various aspects, the present teachings provide a system for adjusting a control of a vehicle system based on a condition of an occupant. The system includes a replaceable or upgradeable electronic skin removably coupled to an interior vehicle component. The electronic skin includes at least one sensor positioned therein, configured to monitor/obtain a biometric, physiological, or wellness condition measurement from the occupant. The system includes one or more processors and a memory communicably coupled thereto. An occupant comfort module is provided including instructions that, when executed, collect and monitor feedback from the at least one sensor; determine that the feedback exceeds a predetermined threshold; and determine an adjustment for a vehicle system based on the feedback. A control module may be provided including instructions that, when executed by the one or more processors, cause the vehicle system to change at least one setting based on the adjustment determined by the occupant comfort module.

In other aspects, the present teachings provide a system for adjusting a control of a vehicle system based on a condition of an occupant within a vehicle or a vehicle diagnostic. The system includes a plurality of electronic skin components configured to be selectively coupled to, and removed from, a plurality of interior vehicle components. Each electronic skin component includes an array of sensors positioned therein to interface with an occupant. The array of sensors is configured to monitor or obtain: (1) a biometric, physiological, or wellness condition measurement from the occupant, and (2) at least one vehicle diagnostic condition. The system includes one or more processors, and a memory communicably coupled to the one or more processors. The memory stores an occupant comfort module. The occupant comfort module includes instructions that, when executed by the one or more processors, cause the one or more processors to: collect and monitor feedback from the array of sensors; determine that at least one of: (1) the biometric, physiological, or wellness condition measurement from the occupant, or (2) the vehicle diagnostic condition exceeds a predetermined threshold; and determine an adjustment for a vehicle system based on the feedback. A control module is provided that includes instructions that, when executed by the one or more processors, causes a change to at least one setting of the vehicle system based on the adjustment determined by the occupant comfort module.

In still other aspects, the present teachings provide a method for controlling a setting of a vehicle system. The method includes collecting and monitoring feedback from at least one sensor that is disposed within an electronic skin. The electronic skin is removably coupled to an interior vehicle component. The at least one sensor is configured to monitor or obtain a biometric, physiological, or wellness condition measurement from an occupant. The method includes determining, using an occupant control module, that the feedback exceeds a predetermined threshold. The method further includes determining, using the occupant control module, an adjustment for a vehicle system based on the feedback. Once the adjustment is determined, the method includes causing, using a vehicle control module, a change to at least one setting of the vehicle system based on the adjustment determined by the occupant comfort module.

Further areas of applicability and various methods of enhancing the above technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein.

Figure 1:
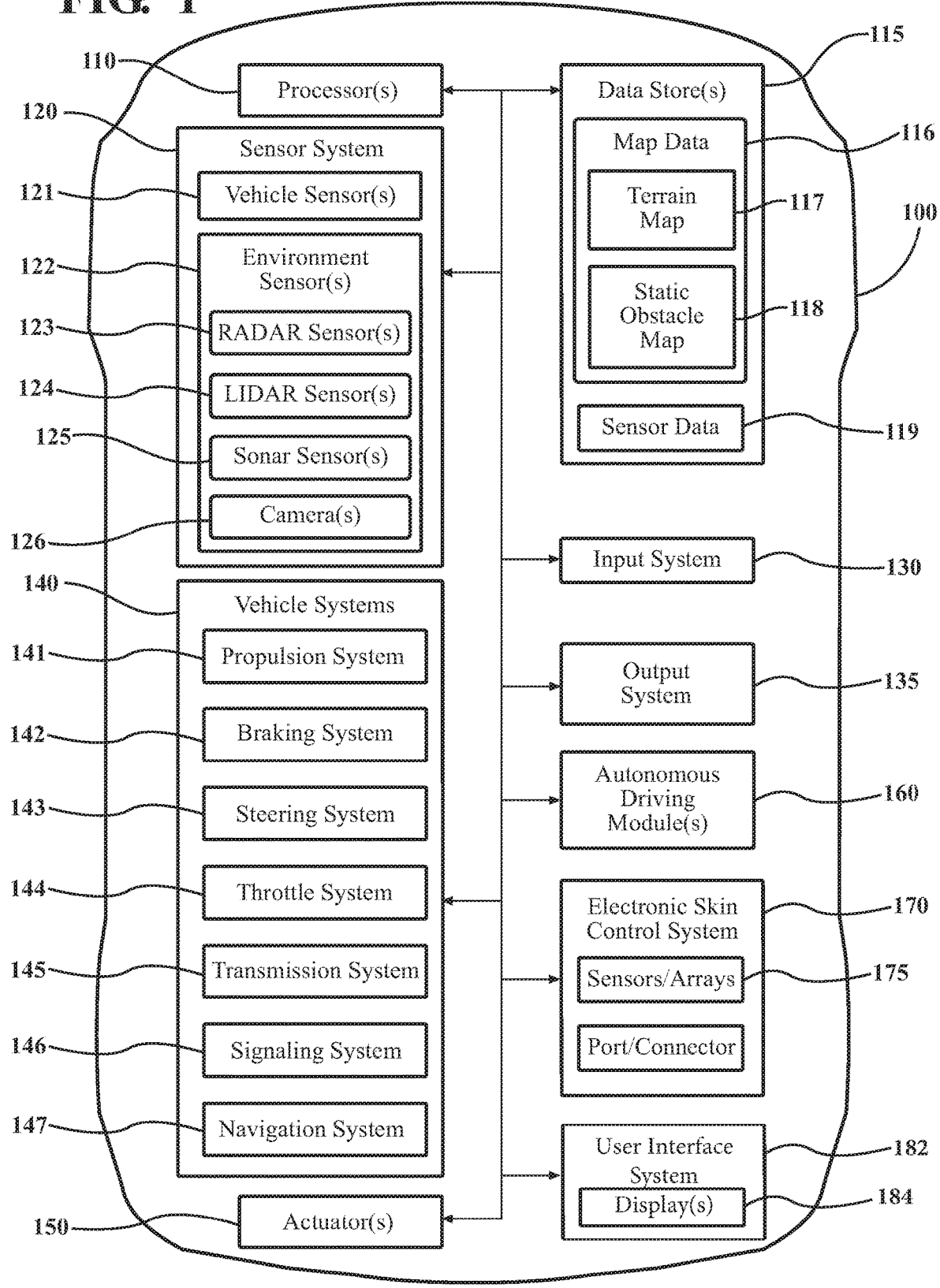
FIG. 1 is a schematic diagram illustrating an exemplary aspect of a vehicle within which systems and methods disclosed herein according to the present technology may be implemented.

It should be noted that the figures set forth herein are intended to exemplify the general characteristics of the methods, algorithms, and devices among those of the present technology, for the purpose of the description of certain aspects. These figures may not precisely reflect the characteristics of any given aspect and are not necessarily intended to define or limit specific embodiments within the scope of this technology. Further, certain aspects may incorporate features from a combination of figures.

DETAILED DESCRIPTION

The present technology generally provides systems and methods for controlling and adjusting various convenience and operational features of a vehicle or vehicle system that may be based, at least in part, on biometric and wellness measurements/conditions of the occupant(s) of the vehicle. The technology provides various interior vehicle components with an outer electronic layer, substrate, or covering that may be referred to in the art as a "robotic skin", "electronic skin", or "e-skin." The substrate, or electronic skin, may include a variety of sensors, such as an array of various sensors configured for sensing data and bioelectronics for human-machine interaction, which can be used to control and adjust the convenience and operational features of the vehicle or vehicle system, including safety features and systems.

Systems and methods are provided for adjusting a control of various vehicle systems based on one or more condition(s) of the occupant. As will be discussed in more detail below, the system includes an electronic skin removably coupled to an interior vehicle component. The electronic skin includes at least one sensor positioned therein, configured to monitor and/or obtain a biometric, physiological, or wellness condition measurement from the occupant. The system includes one or more processors and a memory communicably coupled thereto. An occupant comfort module is provided including instructions that, when executed, perform various tasks. For example, the instructions may include commands or directions to: collect and monitor feedback from the at least one sensor; determine that the feedback exceeds a predetermined threshold; and determine an adjustment for a vehicle system based on the feedback. A control module may be provided including instructions that, when executed by the one or more processors, cause the vehicle system to change at least one setting based on the adjustment determined by the occupant comfort module.

The electronic skin (as well as other components and devices that work with the electronic skin) may generally be provided as a modular component that can be installed, removed, replaced, and/or upgraded. In this regard, the electronic skin, and the various components used therewith, can be installed in a vehicle during its initial production, or as an aftermarket product that may include plug-and-play type components. Thus, the system and can be easily removed should the owner want to sell the vehicle, or transfer and use the system in a different vehicle. As the progression and improvements of technology increase at a fast rate, the modular/wearable nature of the system allows for owners to easily upgrade the different components when desired. The electronic skin can be mechanically coupled, fastened, or otherwise affixed to the vehicle components in various manners, depending on the vehicle component. In certain aspects, at least a portion of the electronic skin may be provided as a permanent portion of a vehicle trim component, fabric, or covering, etc. In various aspects, the electronic skin may generally be provided as a removable cover or outer substrate component for any interior vehicle component within the vehicle that regularly interacts with, for example, makes contact with, a human or animal occupant and a seat, armrest, steering wheel, gear shift, door trim, or other. In this regard, the electronic skin can generally be provided as a flexible substrate with integral sensors that are configured to monitor biometric and wellness measurements/conditions of the occupant. Depending on the particular sensor, the electronic skin may be required to make physical contact with the occupant. In other aspects, indirect contact or interaction with the occupant, for example, through a thin barrier such as a layer of clothing, may be sufficient for the sensor(s) to operate.

One or more controller and/or control module can be used to collect and analyze the data and feedback, and to ultimately control and cause an adjustment to a parameter or setting of a vehicle system that may be considered to be related to the measurement or condition, as will be discussed below. In various aspects, one or more processors are used to determine and provide an adjustment and cause a change to at least one setting of the vehicle system. In various non-limiting examples, the change to at least one setting may include an instruction to modify a setting of at least one of: a vehicle heating, ventilation, and air conditioning (HVAC) system; a vehicle audio system; a vehicle lighting system; a vehicle display system; a vehicle suspension system; and a vehicle seat configuration.

Systems of the present technology may also be configured to sense or otherwise obtain vehicle diagnostic conditions and inform an occupant of issues related to various vehicle systems and parameters. In certain aspects, changes to vehicle systems can be made based on a consideration of a combination of measurements from an occupant in addition to certain vehicle diagnostic conditions and/or measurements. In other aspects, changes to vehicle systems can also include consideration of external environmental factors or metrics, such as weather conditions, traffic conditions, road quality conditions, road types, a location of the vehicle, and current vehicle speed. For example, severe weather situations; heavy traffic; construction zones; roads with pot holes or unpaved or deteriorated areas; travel through unsafe areas; travel in high speed areas; travel adjacent to large vehicles, and the like, may cause an occupant to have increased stress or nervous conditions. Various vehicle systems such as temperature, lighting, music, or a vehicle display can be adjusted to increase occupant alertness and/or make the driving experience more comfortable and pleasing. Having the adjustments made automatically, or autonomously, without a requirement for manual input from an occupant may also allow an occupant to focus on driving and not be distracted with the need to change a setting for a vehicle system.

The various sensors, processors, and modules used with this technology may be provided with wired and/or wireless communication capabilities, and can be used in combination with "smart" personal devices, such as phones, watches, key fobs, and other wearable devices known in the art. Software from the smart personal device can be integrated for use with the systems and technology described herein. The systems and technology can also be used or controlled remotely, for example, controlled at a remote location other than within the vehicle. The electronic skin components may be provided with suitable flexible/conformal antennas, communication components, and communication units that are configured to provide feedback from the sensors to the processors and modules. The electronic skin components may have wired or wireless communication capabilities and means for accessing wired or wireless power via flexible power coils, or the like, for their operation. The electronic skin components may be provided with a plug or connector configured to be received in an appropriate port (e.g., electrical or pneumatic) located adjacent the respective vehicle component or otherwise within the vehicle. In certain aspects, rechargeable batteries or fuel cells can be used as an alternative to using vehicle power. Renewable energy sources, such as solar power, can also be used.

Referring to FIG. 1, an example of a vehicle 100 is illustrated. As used herein, a "vehicle" is any form of motorized transport. In one or more implementations, the vehicle 100 is an automobile. While arrangements will be described herein with respect to automobiles, it will be understood that aspects are not limited to automobiles. In some implementations, the vehicle 100 may be any other form of motorized or electrified transport including, for example, an autonomous aerial vehicle.

The vehicle 100 includes various elements. It will be understood that in various aspects it may not be necessary for the vehicle 100 to have all of the elements shown in FIG. 1. The vehicle 100 can have any combination of the various elements shown in FIG. 1. Further, the vehicle 100 can have additional elements to those shown in FIG. 1. In some arrangements, the vehicle 100 may be implemented without one or more of the elements shown in FIG. 1. While the various elements are shown as being located within the vehicle 100 in FIG. 1, it will be understood that one or more of these elements can be located external to the vehicle 100. Further, the elements shown may be physically separated by large distances. Some of the possible elements of the vehicle 100 are shown in FIG. 1 and will be described along with subsequent figures. However, a description of many of the elements in FIG. 1 will be provided after the discussion of the remaining figures for purposes of brevity of this description.

Figure 2:
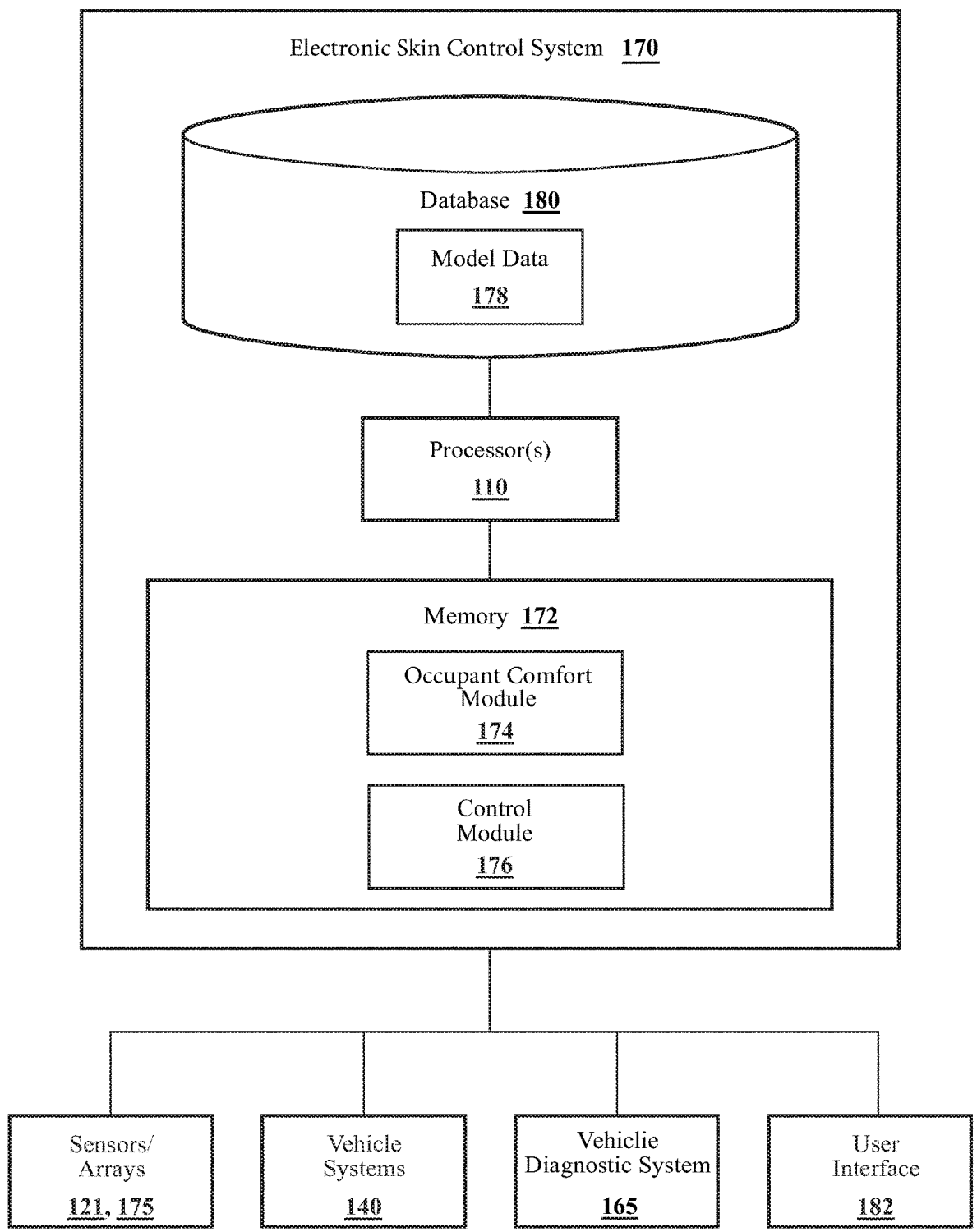
FIG. 2 is a schematic diagram illustrating an exemplary aspect of an electronic skin control system as provided in FIG. 1, with an occupant comfort module.

With reference to FIG. 2, an exemplary electronic skin control system 170 of FIG. 1 is illustrated. The electronic skin control system 170 is implemented to perform methods and other functions as disclosed herein relating to controlling settings and the overall operation of the various vehicle systems 140 based, at least in part, on past, current, observed, or predicted conditions of an occupant within the vehicle 100.

The electronic skin control system 170 is shown as including one or more processors 110 from the vehicle 100 of FIG. 1. The one or more processors 110 may be a part of the electronic skin control system 170; the electronic skin control system 170 may include one or more separate processors from the one or more processors 110 of the vehicle 100; or the electronic skin control system 170 may access the one or more processors 110 through a wireless communication unit, a data bus, or another communication path, depending on the embodiment. In one aspect, the electronic skin control system 170 includes a memory 172 that stores at least an occupant comfort module 174 and a control module 176. The memory 172 may be a random-access memory (RAM), read-only memory (ROM), a hard-disk drive, a flash memory, or other suitable memory for storing the modules 174, 176. The modules 174, 176 are, for example, computer-readable instructions that when executed by the one or more processors 110, cause the one or more processors 110 to perform the various functions disclosed herein.

In connection with controlling settings and/or the operation of vehicle systems 140 of the vehicle 100, the electronic skin control system 170 can store various kinds of model-related data 178 in a database 180. As shown in FIGS. 1-2, the electronic skin control system 170 may receive sensor data from a vehicle sensor system 120 and/or sensors 121, 175 provided as part of the electronic skin control system 170. As also indicated in FIG. 2, the electronic skin control system 170, in particular the control module 176, can communicate directly with the vehicle systems 140 and/or vehicle diagnostic systems 165 to assist with semi-autonomous or autonomous control over various functions of the vehicle 100 and the vehicle systems 140. The control module 176 may also include instructions that cause the one or more processors 110 to control the operation of a user interface system 182 and coordinate the data, including a display of changes in settings and operation of vehicle systems 140, provided to various displays 184 throughout the vehicle 100.

Figure 3:
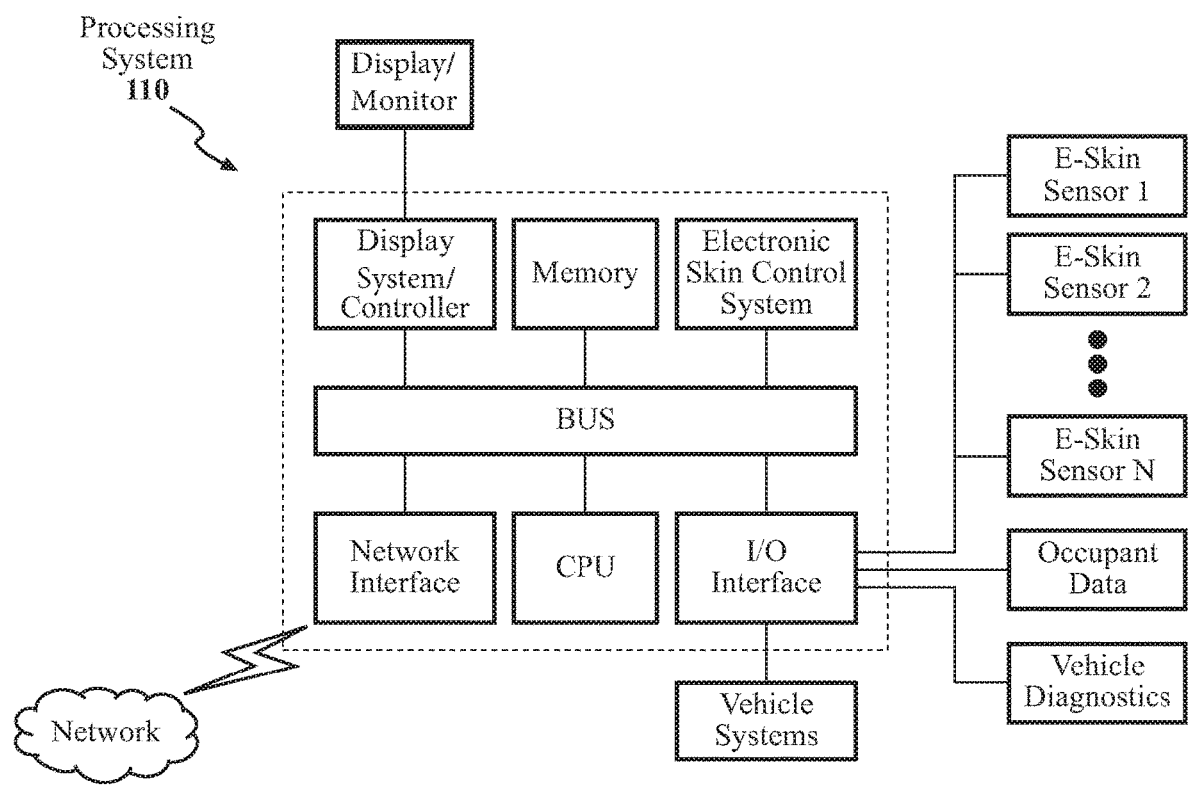
FIG. 3 is another schematic diagram illustrating an exemplary processing system with additional configurations of incorporating an exemplary electronic skin control system with a vehicle.

FIG. 3 is simplified schematic diagram illustrating another arrangement of an exemplary processor, or processing system 110, with additional configurations of incorporating an exemplary electronic skin control system with a vehicle. Various sensors, including a plurality or array of specific sensors located within the electronic skin can be in communication with an I/O interface that can also provide access to occupant data and vehicle diagnostics information, and permit communication to the various vehicle systems. The I/O interface may include a universal serial bus (USB) hub, Bluetooth circuitry, near field communication (NFC) circuitry, or other port or wireless connection disposed within an interior of the vehicle in order to permanently or removably couple with a communication component configured to provide feedback from the sensors of the electronic skin to various other components, including the electronic skin control system 170 and the occupant comfort module 174. The feedback can be provided using a variety of types of signals as known in the art.

Figure 4:
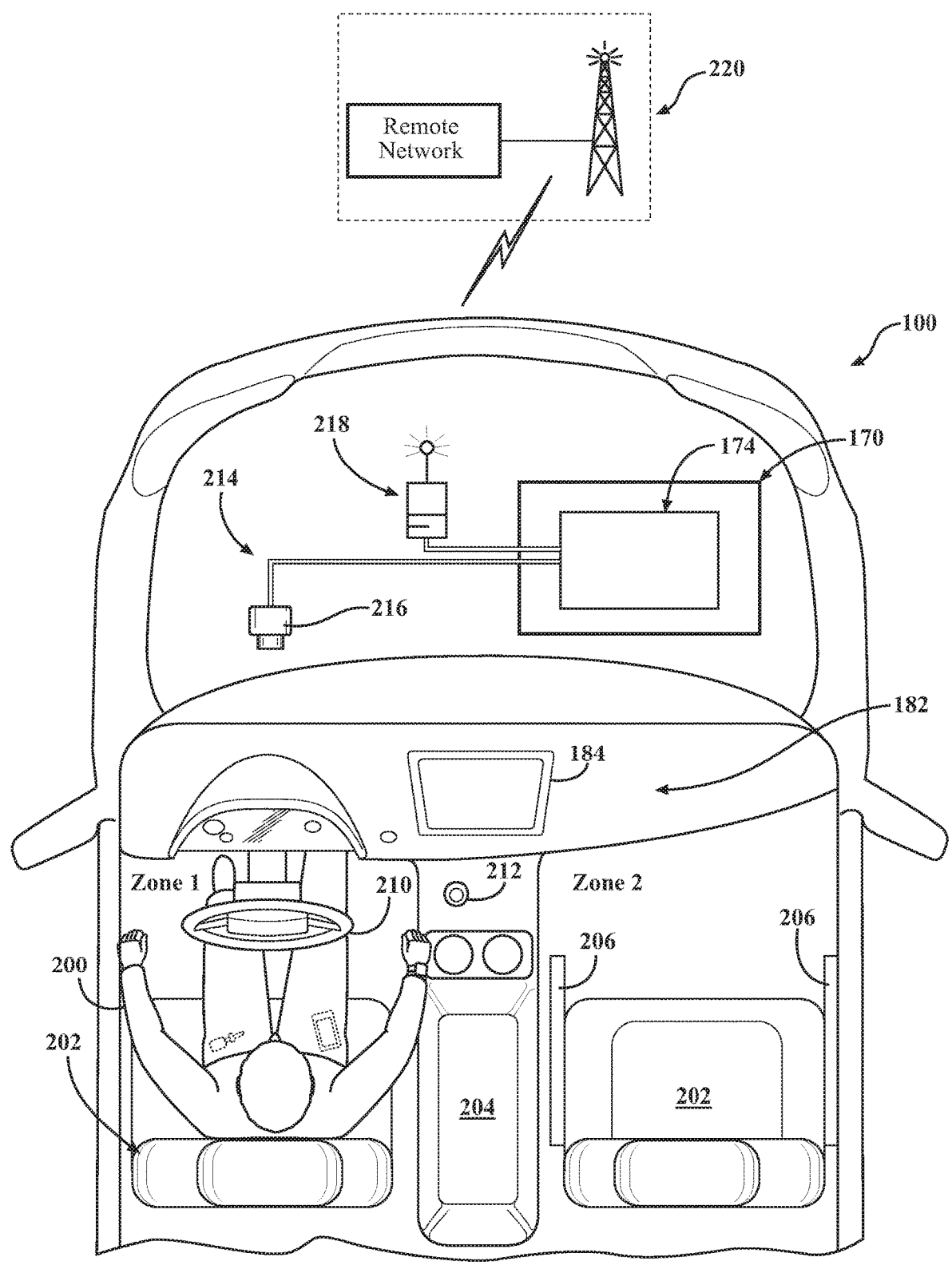
FIG. 4 illustrates a partial top plan view of an interior cabin of an exemplary vehicle interior compartment including interior vehicle components that can be used with the electronic skin.
Figure 5:
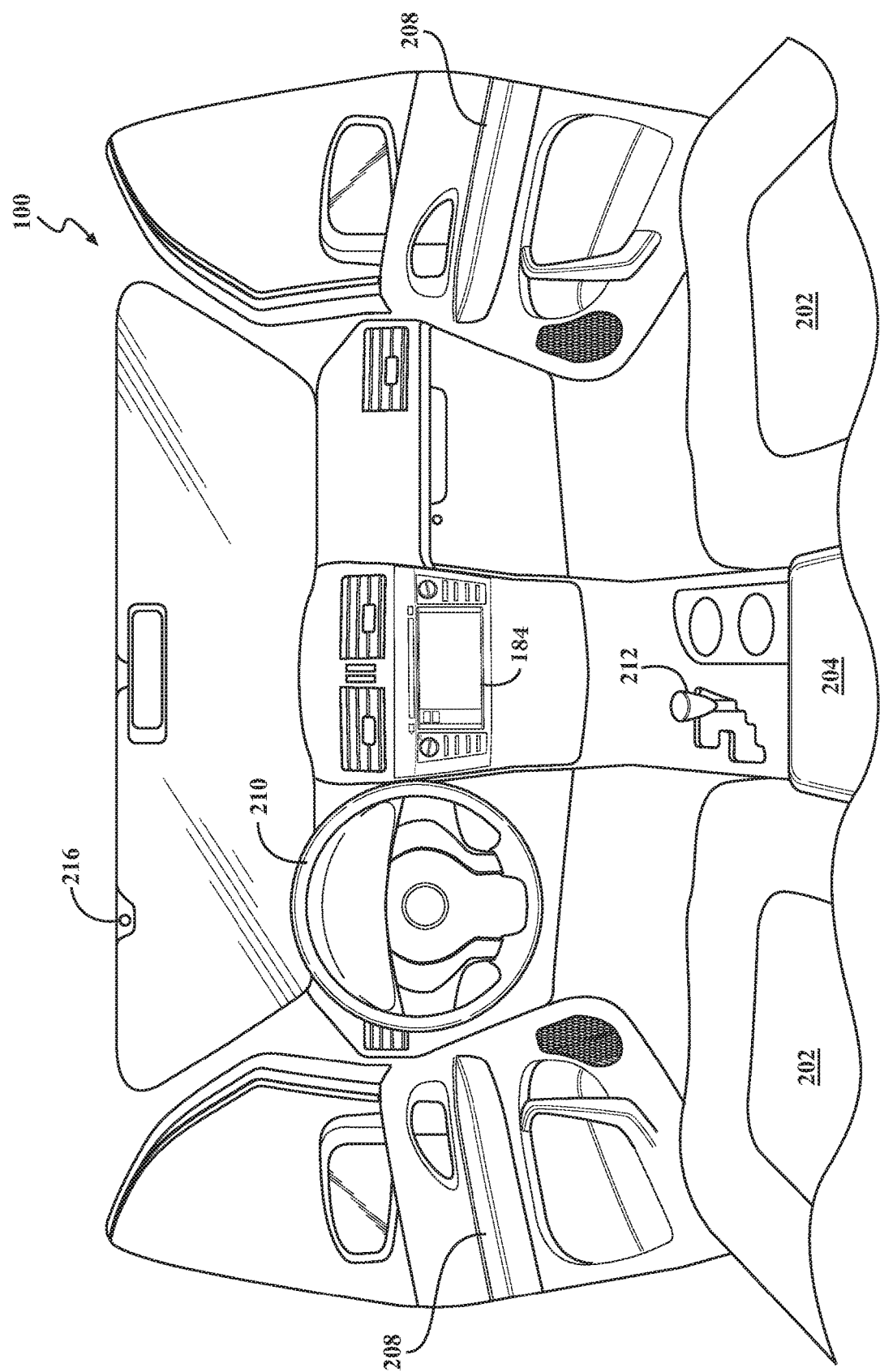
FIG. 5 illustrates a partial perspective view of an interior cabin of an exemplary vehicle interior compartment.

FIG. 4 illustrates a partial top plan view of an interior cabin of an exemplary vehicle interior compartment. FIG. 5 illustrates a partial perspective view of an interior cabin similar to that as provided in FIG. 4. As discussed above, the electronic skin can be configured to be selectively installed and removed from a variety of different interior vehicle components, or portions thereof, that interact with an occupant 200. In this regard, specific non-limiting examples of vehicle components useful with the present technology include a vehicle seat 202; a vehicle console 204, such as a center console; an armrest 206 coupled to a seat (FIG. 4); a door trim element 208 that may be configured as an armrest (FIG. 5); a steering wheel 210; and a gear shift knob 212. Depending on the type of vehicle and interior component configuration, various pillars and flooring areas may also be provided with an electronic skin component. In still other aspects, the present technology can be used with auxiliary seating components. As will be discussed below with respect to FIG. 7, auxiliary seating components such as supplemental seat cushions, child safety seats, child booster seats, and the like, can also be provided with an electronic skin component for various safety and monitoring functions. Various electronic skin components can be independently coupled with or fastened to any combination of vehicle components. Generally, the electronic skin may be color and/or fabric-matched with the vehicle interior, or otherwise designed to blend in with the vehicle aesthetics. Additional sensor systems 214 can be provided within the interior of the vehicle, including cameras 216 and interior radar or lidar plus microphones (not specifically shown). One or more wireless communication unit 218 may be provided to permit wireless communication with the electronic skin components as well as communicate with remote networks and cloud systems 220.

Figure 6:
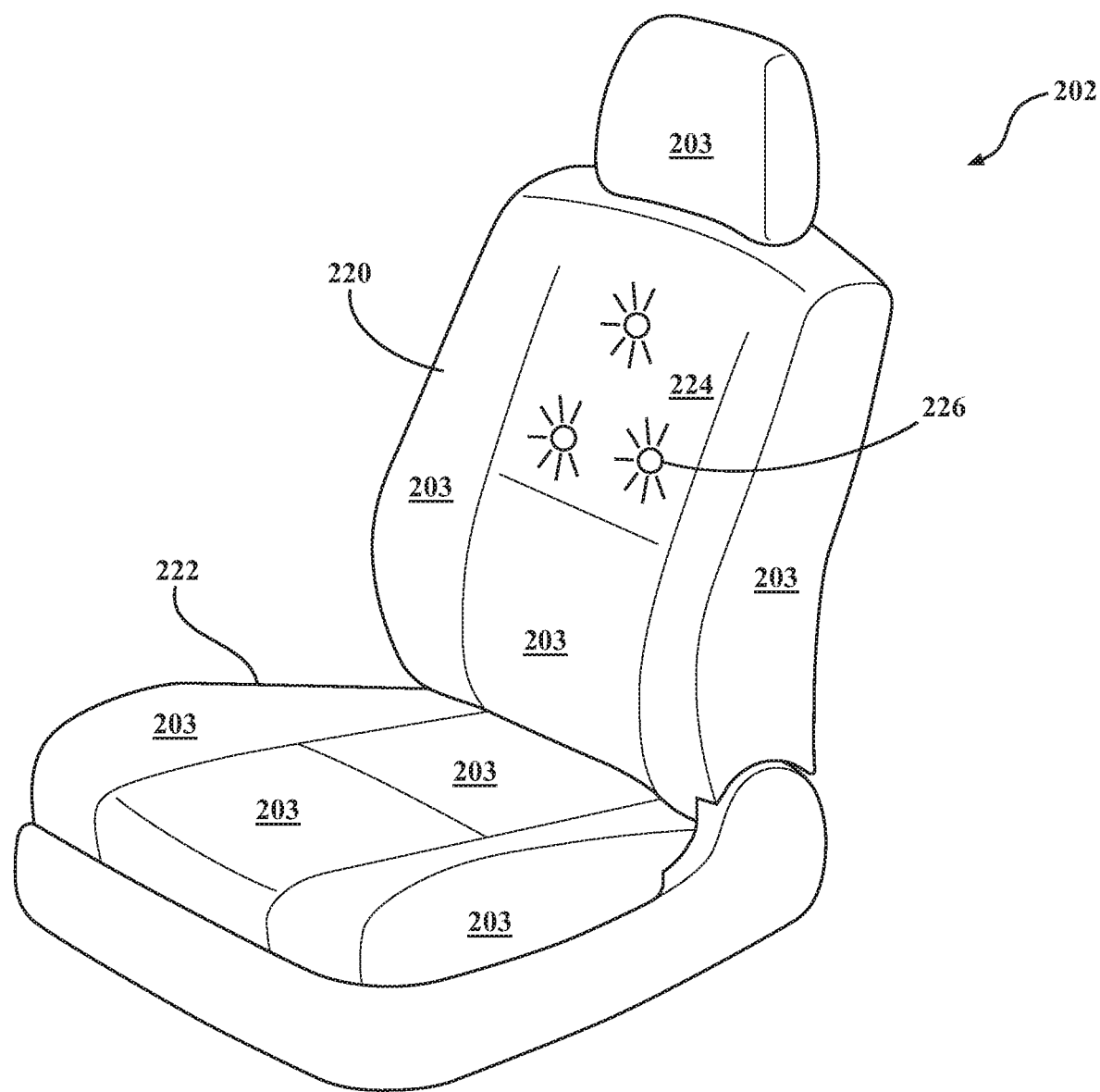
FIG. 6 is a side perspective view of an exemplary vehicle seat configured with an electronic skin including sensors disposed therein according to various aspects of the present teachings.

As a specific example of one implementation of the present technology, FIG. 6 provides a side perspective view of an exemplary vehicle seat 202 shown with different regions 203. The seat 202 is an exemplary vehicle system 140 that can be adjusted by the occupant comfort module 174 or other processing component. Of course, the seat can also be manually adjusted by an occupant. The seat 202 includes an upper portion 220 with at least an adjustable incline, and a lower portion 222 with at least an adjustable height. Suitable motors and/or movement mechanisms (not shown) are provided for adjusting the upper portion 220 and lower portion 222 of the seat 202. At least one region is schematically shown provided with an electronic skin component 224 as a covering over the seat portion and including an array of sensors 226 disposed therein according to various aspects of the present teachings.

Figure 7:
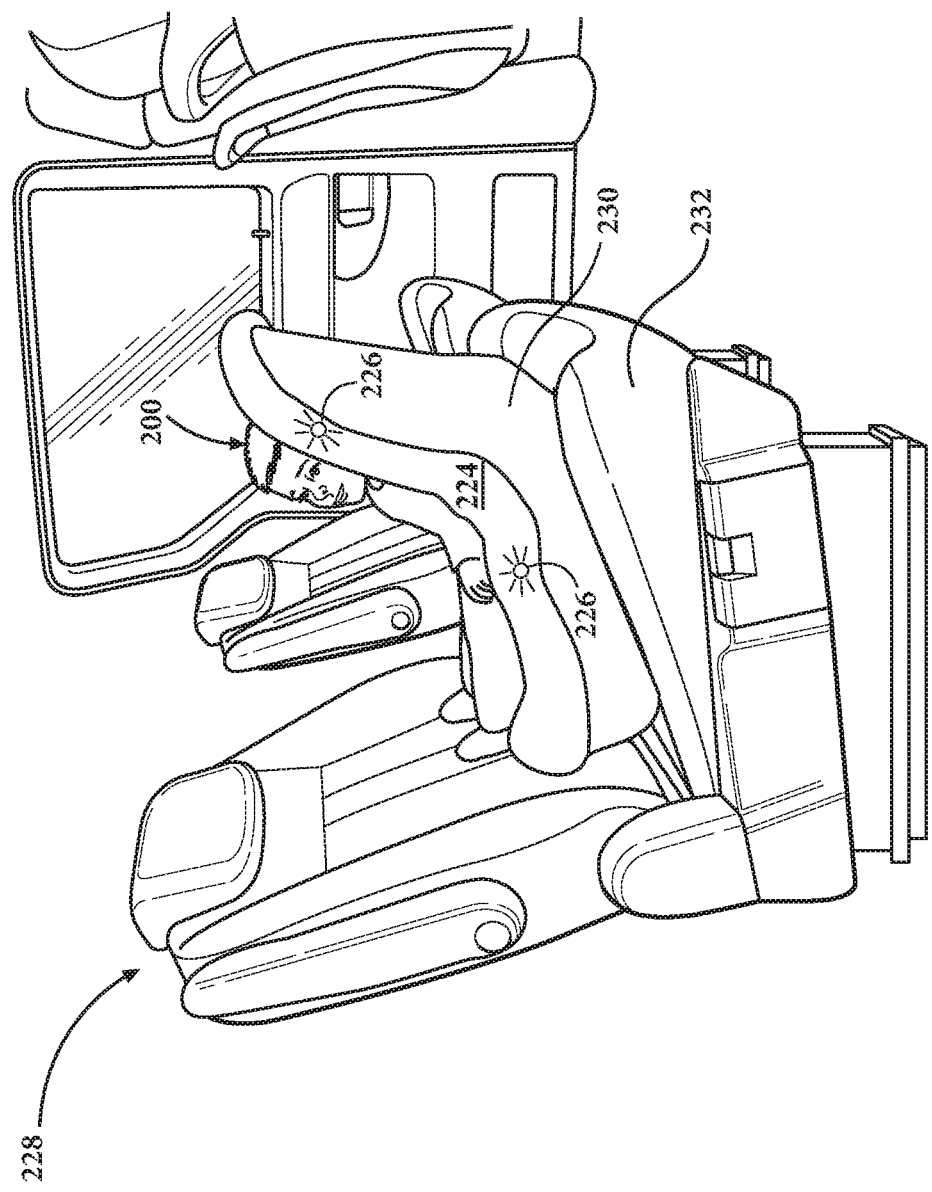
FIG. 7 is a side perspective view of an exemplary vehicle seat with an auxiliary seat component (infant car seat) configured with an electronic skin including sensors disposed therein according to various aspects of the present teachings.

FIG. 7 is a side perspective view of an exemplary vehicle seat 228 disposed in a rear portion of a vehicle cabin provided with an auxiliary seat component 230 configured with an electronic skin 224 including sensors 226 disposed therein according to various aspects of the present teachings. While FIG. 7 specifically provides an exemplary auxiliary seat component 230 configured as an infant car seat coupled to a lower portion 232 of the seat 228, other auxiliary seat components may also be used and provided with configured with a strategically located electronic skin, such as child booster seats, supplemental cushions, massaging or heated cushions, decorative seat covers, and the like. In various aspects, the auxiliary seat component 230 would be provided in communication (wired or wireless) with the occupant comfort module 174 or other processing component.

Various robotic and electronic skins are known in the art and commercially available for use with the present technology. The types of sensors and flexible substrates that can be used in combination to provide an appropriate interaction with an occupant in order to obtain a biometric or wellness condition measurement are continuously being improved and updated; thus, the present technology is not intended to be limited in this regard. Flexible, sensitive, lightweight, and inexpensive known sensors useful in other portable and wearable devices may be well suited for use with the present technology. Typically, the sensors may detect at least one of temperature, pressure, acceleration, optical response, electromagnetic field, electrical resistance, and electrical capacitance. Particularly, integrated wearable sensors have been developed with several different types of transduction systems, such as resistive, capacitive, and piezoelectric sensors. Exemplary electronic skin components can be manufactured by embedding known (or to be discovered) sensors or sensitive layers into electrode-array patterns therein. Electrodes may be discretely embedded in bulk flexible substrate such as polydimethylsiloxane (PDMS) or other flexible rubbers and/or polymers, or the sensors/electrodes may consist of fibers woven into a specific pattern as part of a multi-functional fabric of the skin structure. Three-dimensional structured polymeric materials may also be useful for incorporating highly flexible pressure sensors, and the like. Non-limiting examples of some currently available combinations include an array of ZnO nanorods that may be embedded within a flexible matrix, such as a polyimide; an array of magnetoelectronic sensors that may be embedded within a shapeable nanomembrane; an array of microfluidic pressure sensors that may be embedded within a flexible substrate; an array of electrodes, antennas, power coils, or electrical traces embedded in a bulk flexible polymeric substrate; an array of electrodes, antenna, power coils, or electrical traces comprising conductive fibers woven into a specific pattern as part of a multi-functional fabric of the skin; and any combinations thereof.

It is contemplated that the electronic skin can be used with a wide variety of sensors and/or arrays of sensors in order to obtain the biometric or wellness condition measurements from the occupants. Examples of such sensors include any sensor configured to obtain a physiological attribute of an occupant, as well as sensors capable of determining, or configured to obtain feedback regarding: pulse oximetry readings; blood pressure readings; blood flow readings; blood volume data; EKG wave forms; respiration rates; heart rates; perspiration and the range of associated biosignatures; galvanic skin response readings; electrodermal activity; temperature readings; perspiration readings; pressure readings; vibrational measurements; and other health related information.

In various aspects, the occupant control module 174 is configured to collect, monitor, save, and/or analyze the feedback from the various sensors. The feedback may then be compared to various predetermined threshold values. In certain aspects, the threshold values may be occupant specific and stored in an occupant profile or other data store. Threshold values may be adaptively adjusted over time using machine learning algorithms based on a particular occupant history. If the occupant control module 174, or other suitable processor or module, determines that the feedback exceeds a predetermined value, systems and methods of the present technology provide for the determination of an adjustment to be made to an appropriate vehicle system. Generally, the specific adjustment to a vehicle system is made based on the type of feedback received. For example, feedback regarding occupant temperature, a change in a thermal profile, and/or perspiration may provide the basis for an adjustment to the HVAC system; feedback regarding abrupt occupant pressure changes against the electronic skin of a seat or feedback regarding vibrations may provide the basis for an adjustment to the suspension system; feedback regarding seat pressure may provide the basis for an adjustment to the seating system, such as changing inflation levels of internal chambers; feedback that can be related to, or otherwise indicate, an increased stress level of the occupant, or a decreased level of alertness, may provide the basis for an adjustment to the audio system, a level of interior or exterior lighting, an adjustment of a seat position or configuration, an adjustment of the interior temperature, and the like.

As described above, the system may include a plurality of occupant profiles that may include custom occupant settings. In this regard, the determination of an adjustment for a vehicle system may be made based on a combination of the feedback received from the sensors and the custom occupant settings. For example, certain occupants may prefer only a certain range of interior cabin temperatures; the use of heated/cooled seats; the use of certain suspension modes; seating positions and configurations; seating massage settings; music genres, radio stations, and audio intensity;

lighting modes, intensities, or colors, etc. Certain occupants may respond to adjustments in different ways. For example, certain occupants may become less stressed after an adjustment of the audio system to play classical or soothing music; for other occupants, they may become less stressed in an environment with a cooler temperature after an adjustment of an HVAC setting; for still other occupants, an adjustment to a color or intensity of interior lighting may be calming. In various aspects, the changes to vehicle systems may be made automatically without involvement by the occupant. In certain aspects, the systems and methods may provide a visual or audible notification to the occupant that indicates an adjustment to a vehicle system has been made or will be made. This may include providing an opportunity for the occupant to reject the setting changes or make additional modifications thereto.

With respect to analysis of the feedback related to biometric, physiological, or wellness condition measurements from the occupant, one or more modules of the system may be configured to analyze changes in the feedback over a period of time. The adjustments for the vehicle system may then be based on the changes in feedback that are analyzed over the period of time. For example, in various aspects, the feedback may be indicative that the occupant may have an increased stress level or fatigue level. This may be based on an analysis of a plurality of biometric and wellness condition measurements, or other health metrics over the period of time, such as blood pressure and heart rate, or the detection of cortisol or particular perspiration signatures. In other aspects, this can be determined by feedback indicative of the occupant tightly grasping the steering wheel or gear shift knob. The analysis may also be based on other conditions, such as feedback from sensors external to the electronic skin, including cameras and microphones. For example, certain cameras may be programmed to detect eye gaze, squinting, or pupil size that may be related to occupant focus and attention. In certain situations, the systems can be configured to predict that the stress (or a perceived change in mood) may be for a short period of time, such as stress due to an upcoming merger onto a highway or turn from a busy intersection. The systems may determine that although that type of feedback may generally indicate a need for an adjustment of a vehicle system, the passage of a short period of time may be required prior making an adjustment or modification. In another example, after the passage of the short period of time, further analysis may be performed prior to any adjustment is made. In certain other situations, the systems can predict that the stress may be for a longer period of time, or as part of a trend, which may be based on occupant history or profile data, and adjustments to the vehicle systems are made at a sooner time. The analysis may also be used to determine a level of occupant impairment. For example, various sensors may be used to detect a level of alcohol or substance usage. In another example, sensors may also be configured to detect blood glucose levels from perspiration, which may affect an occupant.

The analysis of the feedback may also include an assessment of reliability of the data. For example, the electronic skin may become worn or damaged over time, which may affect the accuracy of certain of the sensors. In such case, the system may display a message to the user indicating the need for replacement or upgrade of the electronic skin hardware.

In various aspects, the system may include a plurality of electronic skin components coupled to a plurality of different interior vehicle components that are configured to monitor or obtain biometric, physiological, or wellness condition measurements from a respective plurality of occupants in the vehicle. In this regard, the occupant comfort module 174 may be configured to determine an adjustment for a vehicle system for a plurality of zones, with each zone corresponding to a location of a different occupant. For example, FIG. 4 provides a first zone (Zone 1) that may be for a driver occupant, and a second zone (Zone 2) that may be provided for a passenger occupant. This may allow for an adjustment of different settings for the same vehicle system. In the example of an HVAC system, a first occupant may prefer air circulation directed at a specific location, while a second occupant may only prefer actuation of a heated seat. In the example of a seat system, a first occupant may prefer adjustments to a height of the seat, while a second occupant may prefer adjustments to an incline of a seat. Or, in the case of an auxiliary seating component such as a child seat in the rear of the vehicle (FIG. 7), a soothing music may be played locally or aimed/directed to a specific area or occupant, while remaining inaudible to the Zone 1 occupant. Similarly, certain adjustments may be prohibited from being made depending on the zone. For example, the system may prohibit the reclining of a vehicle seat of a driver past a certain angle when not in an autonomous driving mode.

In various aspects, the systems of the present technology, such as the electronic skins and sensors therein, are also capable of performing vehicle diagnostic functions. In this regard, the system modules are also capable of incorporating vehicle diagnostic measurements into determinations regarding adjustments of vehicle settings. In one example, if sensors in an electronic skin disposed on the gear shift knob detect vibrations, and the occupant is not in contact with the gear shift knob, the vibrations may be indicative of an issue or disorder with the transmission of the vehicle. In another example, if sensors in an electronic skin disposed on the steering wheel detect vibrations, and the occupant is not in contact with the steering wheel, or a specific portion thereof, the vibrations may be indicative of an issue or disorder with the tires, wheels, or suspension system. In yet another example, if an electronic skin is in contact with the battery compartment of the vehicle and detects an anomalous temperature it may be indicative of a battery disorder. The occupant comfort module 174 may be configured to determine that a vehicle diagnostic condition exceeds a predetermined threshold and make adjustments to one or more vehicle system accordingly, as well as provide a notification to the occupant regarding the vehicle diagnostic condition.

FIG. 1 will now be discussed in full detail as an example vehicle environment within which the system and methods disclosed herein may operate. In some instances, the vehicle 100 is configured to switch selectively between an autonomous mode, one or more semi-autonomous operational modes, and/or a manual mode. Such switching, also referred to as handover when transitioning to a manual mode, can be implemented in a suitable manner, now known or later developed. "Manual mode" means that all of or a majority of the navigation and/or maneuvering of the vehicle is performed according to inputs received from a user (e.g., human driver/operator).

In one or more aspects, the vehicle 100 is an autonomous vehicle. As used herein, "autonomous vehicle" refers to a vehicle that operates in an autonomous mode. "Autonomous mode" refers to navigating and/or maneuvering the vehicle 100 along a travel route using one or more computing systems to control the vehicle 100 with minimal or no input from a human driver/operator. In one or more aspects, the vehicle 100 is highly automated or completely automated. In one aspect, the vehicle 100 is configured with one or more semi-autonomous operational modes in which one or more computing systems perform a portion of the navigation and/or maneuvering of the vehicle along a travel route, and a vehicle operator (i.e., driver) provides inputs to the vehicle to perform a portion of the navigation and/or maneuvering of the vehicle 100 along a travel route. Thus, in one or more aspects, the vehicle 100 operates autonomously according to a particular defined level of autonomy. For example, the vehicle 100 can operate according to the Society of Automotive Engineers (SAE) automated vehicle classifications 0-5. In one aspect, the vehicle 100 operates according to SAE level 2, which provides for the autonomous driving module 160 controlling the vehicle 100 by braking, accelerating, and steering without operator input but the driver/operator is to monitor the driving and be vigilant and ready to intervene with controlling the vehicle 100 if the autonomous module 160 fails to properly respond or is otherwise unable to adequately control the vehicle 100.

The vehicle 100 can include one or more processors 110. In one or more arrangements, the processor(s) 110 can be a main processor of the vehicle 100. For instance, the processor(s) 110 can be an electronic control unit (ECU). The vehicle 100 can include one or more data stores 115 for storing one or more types of data. The data store 115 can include volatile and/or non-volatile memory. Examples of suitable data stores 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store 115 can be a component of the processor(s) 110, or the data store 115 can be operably connected to the processor(s) 110 for use thereby. The term "operably connected," as used throughout this description, can include direct or indirect connections, including connections without direct physical contact.

In one or more arrangements, the one or more data stores 115 can include occupant data 116. The occupant data 116 can include occupant profiles 117 as well as occupant preferences 118. In various aspects, the occupant profiles 117 can include information regarding the occupant, such as descriptive and/or physical features of height, weight, age, gender, the use of glasses, biometric information, and any other pertinent information. In some instances, the occupant profiles 117 can include various health data. The occupant data 116 can be in any suitable form and may be encrypted for privacy. The occupant preferences 118 can include preferences for a variety of vehicle systems, specifically including HVAC settings, music genre preferences, audio and radio settings, speaker preferences, seat and mirror settings and locations, vehicle suspension settings, types of road and navigation preferences, weather-related preferences and vehicle settings, traffic-related preferences, speed control preferences, and the like.

The one or more data stores 115 can include sensor data 119. In this context, "sensor data" means any information about the sensors that the vehicle 100 is equipped with, including the capabilities and other information about such sensors. As will be explained below, the vehicle 100 can include a vehicle sensor system 120. The sensor data 119 can relate to one or more sensors of the vehicle sensor system 120 as well as one or more electronic skin sensors/arrays 175 of the electronic skin control system 170.

In some instances, at least a portion of the occupant data 116 and/or the sensor data 119 can be located in one or more data stores 115 located onboard the vehicle 100. Alternatively, or in addition, at least a portion of the occupant data 116 and/or the sensor data 119 can be located in one or more data stores 115 that are located remotely from the vehicle 100.

Each of the vehicle sensor system 120 and electronic skin control system 170 can include one or more sensors 121, 175. "Sensor" means any device, component and/or system that can detect, and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process. In arrangements in which the vehicle sensor system 120 and electronic skin control system 170 includes a plurality or array of sensors 121, 175, the sensors 121, 175 can function independently from each other. Alternatively, two or more of the sensors 121, 175 can work in combination with each other. In such a case, the two or more sensors can form a sensor network. The vehicle sensor system 120 and electronic skin control system 170 and/or the one or more sensors 121, 175 can be operably connected to the processor(s) 110, the data store(s) 115, and/or another element of the vehicle 100 (including any of the elements shown in FIGS. 1 and 2). The vehicle sensor system 120 can acquire data of at least a portion of the external environment of the vehicle 100, including data from nearby vehicles.

The vehicle sensor system 120 can include any suitable type of sensor. Various examples of different types of sensors will be described herein. However, it will be understood that the aspects are not limited to the particular sensors described. The vehicle sensor system 120 can include one or more vehicle sensors 121. The vehicle sensor(s) 121 can detect, determine, and/or sense information about the vehicle 100 itself. In one or more arrangements, the vehicle sensor(s) 121 can be configured to detect, and/or sense position and orientation changes of the vehicle 100, such as, for example, based on inertial acceleration. In one or more arrangements, the vehicle sensor(s) 121 can include one or more accelerometers, one or more gyroscopes, an inertial measurement unit (IMU), a dead-reckoning system, a global navigation satellite system (GNSS), a global positioning system (GPS), a navigation system 147, and/or other suitable sensors. The vehicle sensor(s) 121 can be configured to detect, and/or sense one or more characteristics of the vehicle 100. In one or more arrangements, the vehicle sensor(s) 121 can include a speedometer to determine a current speed of the vehicle 100.

Alternatively, or in addition, the vehicle sensor system 120 can include one or more environment sensors 122 configured to acquire, and/or sense driving environment data. "Driving environment data" includes and data or information about the external environment in which an autonomous vehicle is located or one or more portions thereof. For example, the one or more environment sensors 122 can be configured to detect, quantify and/or sense obstacles or road conditions in at least a portion of the external environment of the vehicle 100 and/or information/data about such obstacles or road conditions. The one or more environment sensors 122 can be configured to detect, measure, quantify and/or sense other things in the external environment of the vehicle 100, such as, for example, lane markers, signs, traffic lights, traffic signs, lane lines, crosswalks, curbs proximate the vehicle 100, off-road objects, etc.

The vehicle sensor system 120 can include operator sensors that function to track or otherwise monitor aspects related to the driver/operator or occupant(s) of the vehicle 100. In one or more arrangements, the vehicle sensor system 120 can include one or more radar sensors 123, one or more LIDAR sensors 124, one or more sonar (ultrasonic) sensors 125, and/or one or more cameras 126. In one or more arrangements, the one or more cameras 126 can be high dynamic range (HDR) cameras, infrared (IR) cameras and so on. In one aspect, the cameras 126 include one or more cameras disposed within a passenger compartment of the vehicle for performing eye-tracking on the operator/driver in order to determine a gaze of the operator/driver, an eye track of the operator/driver, and so on.

The vehicle 100 can include an input system 130. An "input system" includes any device, component, system, element or arrangement or groups thereof that enable information/data to be entered into a machine. The input system 130 can receive an input from a vehicle passenger (e.g. a driver or a passenger). The vehicle 100 can include an output system 135. An "output system" includes any device, component, or arrangement or groups thereof that enable information/data to be presented to a vehicle passenger (e.g. a person, a vehicle passenger, etc.).

The vehicle 100 can include one or more vehicle systems 140. Various examples of the one or more vehicle systems 140 are shown in FIG. 1. However, the vehicle 100 can include more, fewer, or different vehicle systems. It should be appreciated that although particular vehicle systems are separately defined, each or any of the systems or portions thereof may be otherwise combined or segregated via hardware and/or software within the vehicle 100. The vehicle 100 can include a propulsion system 141, an HVAC system 142, a steering system 143, an audio system 144, a transmission system 145, a suspension system 146, and/or a navigation system 147. A user interface system 182 can also be provided that can be used with various displays and/or display systems 184. For example, the display system 184 can include one or more 2-D panel displays, 3-D volumetric displays, holographic displays, or the like. Each of these systems can include one or more devices, components, and/or combination thereof, now known or later developed.

The processor(s) 110, the electronic skin control system 170, the occupant comfort module 174, and/or the control module 176 can be operably connected to communicate with the various vehicle systems 140 and/or individual components thereof. For example, the processor(s) 110 and/or the occupant comfort module 174 can be in communication to send and/or receive information from the various vehicle systems 140 to control or cause the movement, speed, maneuvering, heading, direction, etc. of the vehicle 100. The processor(s) 110, the electronic skin control system 170, and/or the occupant comfort module 174 may control some or all of these vehicle systems 140 and, thus, may be partially or fully autonomous. As used herein, "cause" or "causing" means to make, force, compel, direct, command, instruct, and/or enable an event or action to occur or at least be in a state where such event or action may occur, either in a direct or indirect manner.

The vehicle 100 can include one or more actuators 150. The actuators 150 can be any element or combination of elements operable to modify, adjust and/or alter one or more of the vehicle systems 140 or components thereof responsive to receiving signals or other inputs from the processor(s) 110 and/or the electronic skin control system 170, the occupant comfort module 174. Any suitable actuator can be used. Non-limiting examples of the one or more actuators 150 can include motors, pneumatic actuators, hydraulic pistons, relays, solenoids, and/or piezoelectric actuators, and control knobs/switches.

The vehicle 100 can include one or more modules, at least some of which are described herein. The modules can be implemented as computer-readable program code that, when executed by a processor 110, implement one or more of the various processes described herein. One or more of the modules can be a component of the processor(s) 110, or one or more of the modules can be executed on and/or distributed among other processing systems to which the processor(s) 110 is operably connected. The modules can include instructions (e.g., program logic) executable by one or more processor(s) 110. Alternatively, or in addition, one or more data store 115 may contain such instructions. Generally, the term module, as used herein, includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

Detailed aspects are disclosed herein. However, it is to be understood that the disclosed aspects are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various aspects are shown in the collective figures, but the aspects are not limited to the illustrated structure or application.

The flowcharts and block diagrams in the figures illustrate the architecture, functionality, and operation of possible implementations of systems, methods and computer program products according to various aspects. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The foregoing description is provided for purposes of illustration and description and is in no way intended to limit the disclosure, its application, or uses. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

As used herein, the phrase at least one of A, B, and C should be construed to mean a logical (A or B or C), using a non-exclusive logical "or." It should be understood that the various steps within a method may be executed in different order without altering the principles of the present disclosure. Disclosure of ranges includes disclosure of all ranges and subdivided ranges within the entire range, including the endpoints.

The headings (such as "Background" and "Summary") and sub-headings used herein are intended only for general organization of topics within the present disclosure, and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment or particular system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

What is claimed is:

1. A system for adjusting a control of a vehicle system based on a condition of an occupant within a vehicle, the system comprising:
    a replaceable electronic skin removably coupled to an interior vehicle component, the electronic skin comprising at least one of a flexible rubber substrate and a flexible polymer substrate, and at least one sensor positioned therein and configured to monitor or obtain a biometric, physiological, or wellness condition measurement from an occupant, the at least one sensor comprising at least one of an array of ZnO nanorods embedded within a flexible polyimide matrix, an array of magnetoelectronic sensors embedded within a shapeable nanomembrane, an array of microfluidic pressure sensors, an array of electrodes, antennas, power coils, or electrical traces embedded in a bulk flexible polymeric substrate, and an array of electrodes, antenna, power coils, or electrical traces comprising conductive fibers woven into a specific pattern as part of a multi-functional fabric of the electronic skin;

one or more processors;

a memory communicably coupled to the one or more processors and storing:

an occupant comfort module including instructions that when executed by the one or more processors cause the one or more processors to:

collect and monitor feedback from the at least one sensor;

determine that the feedback exceeds a predetermined threshold; and determine an adjustment for a vehicle system based on the feedback;

a communication component removably coupled to a port disposed within an interior of the vehicle, the communication component configured to provide the feedback from the at least one sensor to the occupant comfort module; and a control module including instructions that, when executed by the one or more processors, causes a change to at least one setting of the vehicle system based on the adjustment determined by the occupant comfort module.

2. The system according to claim 1, wherein the electronic skin is configured to be selectively installed and removed from a vehicle component selected from the group consisting of: a vehicle seat, an armrest, a vehicle console; a door trim element; a steering wheel; an auxiliary seating component; and a gear shift knob.

3. The system according to claim 1, wherein the communication component is configured to provide a wireless communication between the sensor and the occupant comfort module.

4. The system according to claim 1, wherein the occupant comfort module includes further instructions to:

analyze changes in feedback related to the biometric or wellness condition measurements over a period of time; and determine the adjustment for the vehicle system based on the changes in feedback over the period of time.

5. The system according to claim 4, wherein the occupant comfort module includes further instructions to:

determine a change in a stress level of the occupant based on a plurality of biometric or wellness condition measurements over the period of time; and determine the adjustment for the vehicle system based on the change in the stress level.

6. The system according to claim 1, wherein the electronic skin is configured to obtain a biometric or wellness condition measurement from the occupant selected from the group consisting of: a pulse oximetry reading; a blood pressure reading; a respiration rate; a temperature; a pressure exerted between the occupant and the interior vehicle component; a perspiration reading; and combinations thereof.

7. The system according to claim 1, wherein at least a portion of the electronic skin is in physical contact with the occupant.

8. The system according to claim 1, wherein the instructions to cause the vehicle system to change at least one setting comprises an instruction to:

modify a setting of at least one of:

a vehicle heating, ventilation, and air conditioning (HVAC) system;

a vehicle audio system;

a vehicle lighting system;

a vehicle suspension system;

a vehicle seat configuration; and a vehicle display system.

9. The system according to claim 1, wherein the occupant comfort module is further configured to monitor at least one external environmental metric selected from the group consisting of: weather conditions; traffic conditions; road quality conditions, road type; vehicle location; and vehicle speed.

10. The system according to claim 1, comprising:

a plurality of electronic skins coupled to a plurality of interior vehicle components configured to monitor or obtain biometric, physiological, or wellness condition measurements from a respective plurality of occupants, wherein the occupant comfort module is configured to determine an adjustment for a vehicle system for a plurality of zones, with each zone corresponding to a location of a different occupant.

11. The system according to claim 1, wherein the occupant comfort module:

comprises a plurality of occupant profiles including custom occupant settings; and determines the adjustment for the vehicle system based on a combination of the feedback and the custom occupant settings.

12. The system according to claim 1, wherein the occupant comfort module includes further instructions to:

provide at least one of a visual and audible notification to the occupant indicating the adjustment for the vehicle system.

13. A system for adjusting a control of a vehicle system based on a condition of an occupant within a vehicle or a vehicle diagnostic, the system comprising:

an electronic skin substantially covering an interior vehicle component, the electronic skin comprising a communication component removably coupled to a port disposed within an interior of the vehicle;

a plurality of electronic skin components embedded in the electronic skin and configured to be selectively coupled to, and removed from, a plurality of interior vehicle components, each electronic skin component comprising an array of sensors positioned therein to interface with an occupant and configured to monitor or obtain: (1) a biometric, physiological, or wellness condition measurement from the occupant, and (2) at least one vehicle diagnostic condition, the array of sensors comprising at least one of:

an array of ZnO nanorods embedded within a flexible polyimide matrix;

an array of magnetoelectronic sensors embedded within a shapeable nanomembrane;

an array of microfluidic pressure sensors;

an array of electrodes, antennas, power coils, or electrical traces embedded in a bulk flexible polymeric substrate; and an array of electrodes, antenna, power coils, or electrical traces comprising conductive fibers woven into a specific pattern as part of a multi-functional fabric of the electronic skin;
one or more processors;
a memory communicably coupled to the one or more processors and storing:
an occupant comfort module including instructions that when executed by the one or more processors cause the one or more processors to:
collect and monitor feedback from the array of sensors via the communication component configured to provide the feedback from the array of sensors to the occupant comfort module;
determine that at least one of: (1) the biometric, physiological, or wellness condition measurement from the occupant, or (2) the vehicle diagnostic condition exceeds a predetermined threshold; and
determine an adjustment for a vehicle system based on the feedback; and
a control module including instructions that, when executed by the one or more processors, causes a change to at least one setting of the vehicle system based on the adjustment determined by the occupant comfort module.

14. The system according to claim 13, wherein the plurality of interior vehicle components includes at least one of a steering wheel and a gear shift knob, and the at least one vehicle diagnostic condition is related to a disorder regarding at least one of a suspension system, a wheel, and a transmission system.

15. The system according to claim 14, wherein the occupant comfort module includes further instructions to:
provide at least one of a visual and audible notification to the occupant indicating the vehicle diagnostic condition and disorder.

16. The system according to claim 13, wherein the instructions to cause the vehicle system to change at least one setting comprises an instruction to:
modify a setting of at least one of:
a vehicle heating, ventilation, and air conditioning (HVAC) system;
a vehicle audio system;
a vehicle lighting system;
a vehicle suspension system;
a vehicle seat configuration; and
a vehicle display system.

17. The system according to claim 13, wherein the occupant comfort module includes further instructions to determine the adjustment for the vehicle system based on changes in the feedback over a period of time.

18. The system according to claim 17, wherein the occupant comfort module includes further instructions to:
determine a change in a stress level of the occupant based on a plurality of biometric or wellness condition measurements over the period of time; and
determine the adjustment for the vehicle system based on the change in the stress level.

19. The system according to claim 13, wherein the electronic skin is configured to obtain a biometric or wellness condition measurement from the occupant selected from the group consisting of: a pulse oximetry reading; a blood pressure reading; a respiration rate; a temperature; a pressure exerted between the occupant and the interior vehicle component; a perspiration reading; and combinations thereof.

20. The system according to claim 13, wherein at least a portion of the electronic skin is in physical contact with the occupant.

* * * * *